(12) United States Patent  
Marin

(10) Patent No.: US 7,806,843 B2  
(45) Date of Patent: Oct. 5, 2010

(54) EXTERNAL FIXATOR ASSEMBLY

(76) Inventor: Luis E. Marin, 13825 NW. 22 St., Sunrise, FL (US) 33323-5303

( * ) Notice: Subject to any disclaimer, the term of this patent is extended or adjusted under 35 U.S.C. 154(b) by 107 days.

(21) Appl. No.: 11/903,834

(22) Filed: Sep. 25, 2007

(65) Prior Publication Data

US 2009/0082709 A1  Mar. 26, 2009

(51) Int. Cl.
*A61F 5/00* (2006.01)

(52) U.S. Cl. ............................ 602/27; 606/54

(58) Field of Classification Search .............. 606/54, 606/56–57, 240–241; 602/23, 27
See application file for complete search history.

(56) References Cited

U.S. PATENT DOCUMENTS

| | | | |
|---|---|---|---|
| 2,020,262 A | 11/1935 | Longfellow | |
| 2,035,952 A | 3/1936 | Ettinger | |
| 2,079,567 A | 5/1937 | Anderson | |
| 2,393,831 A * | 1/1946 | Stader | 606/56 |
| 2,406,987 A | 9/1946 | Anderson | |
| 3,941,123 A | 3/1976 | Volkov et al. | |
| 4,176,627 A | 12/1979 | Bassi | |
| 4,308,863 A | 1/1982 | Fischer | |
| 4,338,927 A * | 7/1982 | Volkov et al. | 606/56 |
| 4,535,763 A | 8/1985 | Jaquet | |
| 4,607,625 A | 8/1986 | Schenck | |
| 4,624,249 A | 11/1986 | Alvarez Cambras | |
| 4,696,293 A | 9/1987 | Ciullo | |
| 4,768,524 A | 9/1988 | Hardy | |
| 5,062,844 A | 11/1991 | Jamison et al. | |
| 5,067,954 A | 11/1991 | Ilizarov | |
| 5,087,258 A | 2/1992 | Schewior | |
| 5,496,319 A | 3/1996 | Allard et al. | |
| 5,540,686 A | 7/1996 | Zippel et al. | |
| 5,578,041 A | 11/1996 | Nash et al. | |
| 5,702,389 A | 12/1997 | Taylor et al. | |
| 5,743,898 A | 4/1998 | Bailey et al. | |
| 5,776,132 A | 7/1998 | Blyakher | |
| 5,931,837 A | 8/1999 | Marsh et al. | |
| 6,030,386 A | 2/2000 | Taylor et al. | |
| 6,328,737 B1 | 12/2001 | Moorcroft et al. | |
| 6,461,358 B1 | 10/2002 | Faccioli et al. | |
| 6,964,663 B2 | 11/2005 | Grant et al. | |
| 7,025,790 B2 | 4/2006 | Parks et al. | |
| 7,048,735 B2 | 5/2006 | Ferrante et al. | |

(Continued)

FOREIGN PATENT DOCUMENTS

WO   WO 2007/067297 A2   6/2007

(Continued)

*Primary Examiner*—Michael A. Brown
(74) *Attorney, Agent, or Firm*—Malloy & Malloy, P.A.

(57) ABSTRACT

An external fixator assembly structured for placement and use substantially adjacent the ankle area of the body and including a support assembly comprising at least one base segment and one or two contoured segments disposed substantially on opposite sides of the ankle area. Each of the contoured segments includes a contoured portion having a either different or substantially equivalent angular and/or convergent configurations disposed along a length or height of the ankle area. At least one transfixtion member may be connected along the length of the contoured portion(s) as well as a remainder of the contoured segment(s) so as to extend transversly inward there from into operative engagement with tissue associated with the ankle area patient's body.

30 Claims, 5 Drawing Sheets

U.S. PATENT DOCUMENTS

| | | |
|---|---|---|
| 7,189,237 B2 | 3/2007 | Huebner |
| 7,361,176 B2 | 4/2008 | Cooper et al. |
| 7,422,593 B2 * | 9/2008 | Cresina et al. ............... 606/54 |
| 2004/0138659 A1 | 7/2004 | Austin et al. |
| 2005/0149018 A1 | 7/2005 | Cooper et al. |
| 2005/0251135 A1 | 11/2005 | Riccione et al. |
| 2007/0255280 A1 | 11/2007 | Austin et al. |
| 2009/0082709 A1 | 3/2009 | Marin |
| 2009/0177197 A1 | 7/2009 | Marin |

FOREIGN PATENT DOCUMENTS

| | | |
|---|---|---|
| WO | WO 2007067297 A2 * | 6/2007 |
| WO | WO 2009/042167 A1 | 4/2009 |

* cited by examiner

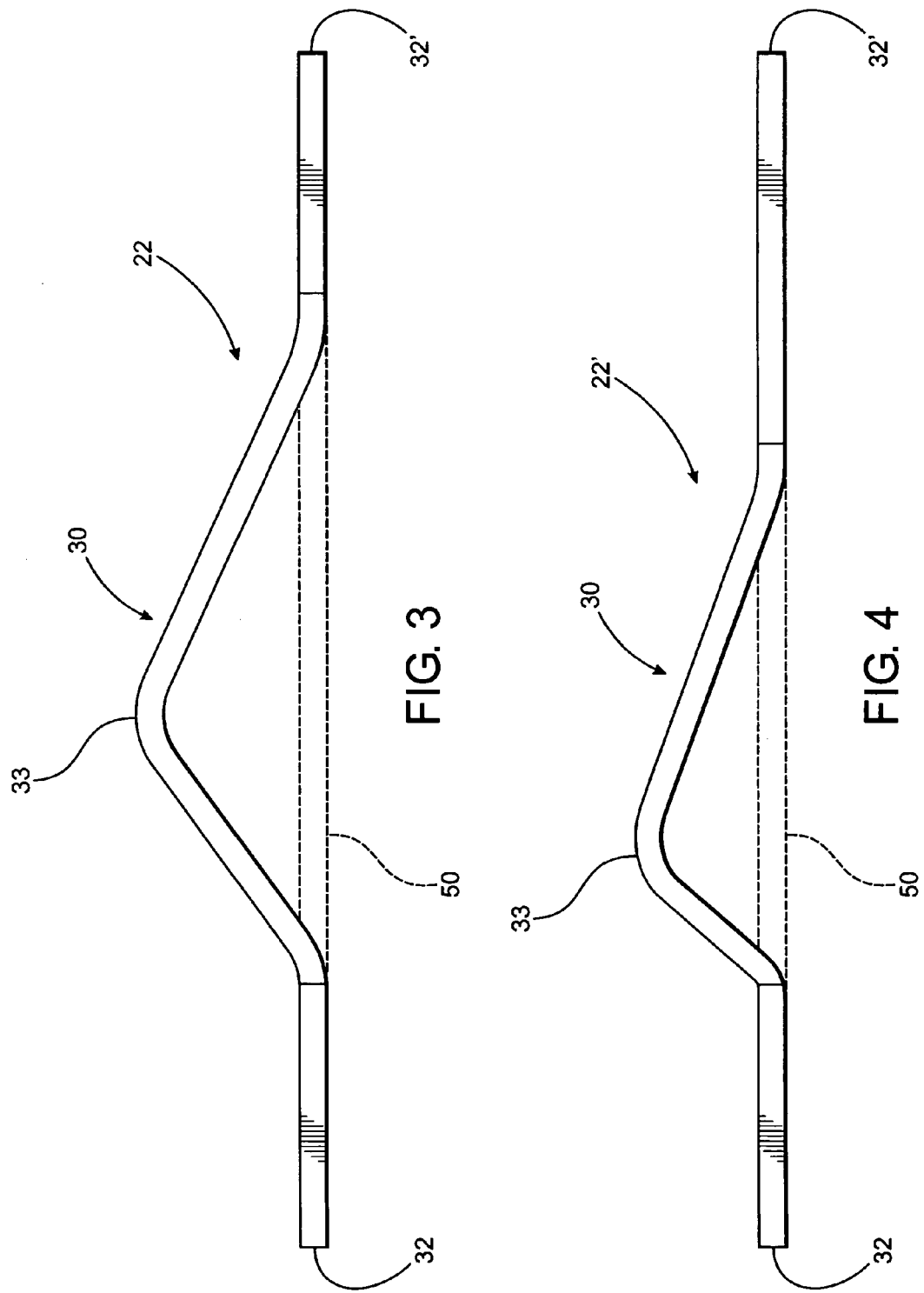

EXTERNAL FIXATOR ASSEMBLY

BACKGROUND OF THE INVENTION

1. Field of the Invention

This invention is directed to an external fixator assembly structured for operative placement relative to and treatment of the ankle area including the ankle joint, foot and correspondingly disposed lower leg bones. A support assembly comprises a base segment configured to at least partially surround the ankle area and one or more contoured segments each including a contoured portion. The contoured portion extends transversely outward from its contoured segment, along a length or height of the ankle or talus area and is structured to dispose one or more transfixion pins at any of a plurality of preferred orientations to engage and efficiently stabilize predetermined portions of the ankle area.

2. Description of the Related Art

In the medical treatment of pathologies including, but not limited to, injuries, fractures, etc. to the bone and joints, external fixator assemblies are commonly used to maintain segments of the bone in an intended and/or required stabilized orientation. By way of example, fixator assemblies of the type described may be utilized to treat the fusion of bone tissue as well soft tissue injuries, and situations involving a union of bones which otherwise are difficult to heal. As such, known or conventional fixator assemblies vary in structure, dimension and configuration and are correspondingly adapted to be used with various portions of the body to which they are attached.

Typical fixator structures include one or more connecting bars or rods as well a plurality of clamps for adjustably securing fixation pins, wires, etc. to the bone portions being affected. Further, transfixion pins or wires of the types commonly utilized may extend completely through the bony tissue or may be anchored therein, such as when the long bones of the leg are involved directly or indirectly with the treatment or healing procedure. Further, the term "transfixion members" is generally recognized in the medical field as describing elongated pins which extend completely or at least partially through the bony tissue involved. In contrast, smaller, thicker "half pins" may be utilized in substantially the same manner to stabilize affected tissue but are of a length insufficient to extend completely through the affected bone, joint, etc. This term may also be used in a more generic sense in referring to stabilizing devices, other than pins, such as wires, reduction wires, screws, clamps, etc.

In addition, known external fixator assemblies of the type described may also include support rings which encircle a corresponding body member, wherein such rings or like support members serve as a supportive base to facilitate proper location of the aforementioned transfixion members. Accordingly, it is commonly understood in the medical profession that fixator assemblies are used to maintain proper-orientation of one or more of bones or bone segments relative to one another to facilitate healing or alignment.

However, the proper stabilization of tissue typically associated with the joint areas of a patient's body such as, but not limited to, the ankle joint as well as the wrist and other smaller bones associated with the hand involves additional considerations. In particular when dealing with the ankle area and the associated tissue serving to interconnect the foot to the lower portion of the leg, the fixator clamps or fixation clamps support blocks are frequently connected to an encircling halo-ring or like support member. These devices are mounted on the ring or other support member to properly position a transfixion pin or like member at a proper height or corresponding distance above the supporting ring in order to engage and thereby properly orient the affected bones of the ankle joint to the foot. In utilizing these support blocks, transfixion clamps, etc., one commonly recognized problem or disadvantage associated therewith is the possibility of these devices obscuring important or necessary portions of the ankle joint when X-rayed. In addition, the proper placement of one or more of such clamps, support blocks, etc. is time consuming for medical personnel and may lack a certain versatility and/or accuracy associated with the accurate placement of a transfixion pin or like transfixion member in the fixed orientation or otherwise support of the various bones of the ankle joint.

Accordingly, there is a need in the medical profession for an external fixator assembly which more efficiently stabilizes or otherwise serves to operatively orient the components and tissue associated with the foot and ankle areas and/or the associated bones of the lower leg corresponding to a connection with the ankle area joint and the foot.

SUMMARY OF THE INVENTION

This invention is directed to an external fixator assembly primarily, but not exclusively, structured for placement adjacent an ankle area of the body. As referred to herein, the term "ankle area" is intended to describe the ankle joint, as well as bones and associated tissue of the foot and lower portions of the leg bones including the fibula and tibia. Further, in properly describing the intended position and orientation of the various preferred embodiments of the external fixator assembly of the present invention, terminology including "length of the ankle area" and/or "height of the ankle area" may be utilized synonymously. These terms are meant to refer to the general distance between the bottom of the foot and an area of the lower part of the leg above the ankle joint. Further the ankle area, as used herein, is meant to be descriptive of the bones and other tissue associated with the foot, ankle joint and lower leg which serve to facilitate the functioning of the ankle joint and intended, relative movements of the corresponding foot and leg connected to the ankle joint.

Accordingly, the external fixator assembly of the present invention comprises a support assembly intended to be disposed adjacent the ankle area and structured to support at least one transfixion pin or like transfixion member in operative engagement with the bones or other associated tissue associated with the ankle area. As such, the support assembly includes at least one base segment preferably, but not necessarily having a curvilinear configuration substantially in the form of an arc and/or semi-circle operatively disposed at the medial and lateral longitudinal segments (?).

In addition, the support assembly includes at least one, and in some applications at least two elongated contoured segments connected to the base segment, which could also be accurately described and/or referred to as a contoured anatomical foot plate. Each of the one or more contoured segments includes a contoured portion, dimensioned and configured to medically imitate the arch of the foot. Further, the contoured portion is disposed along the length of the corresponding contoured segment and extends transversely outward from a remainder of the length of the contoured segment. Accordingly, when properly positioned adjacent the ankle area, the contoured portion extends transversly outward from its contoured segment and adjacent to and along the length or height of the ankle area. Moreover, each contoured portion includes what may be generally referred to as an angular configuration, which in turn may be more specifically defined by a substantially convergent configuration. Accordingly, the angular or convergent configuration of each contoured portion includes an apex or the like structure representing the maximum outward extension of the contoured portion from a remainder of the length of the corresponding contoured segment.

Further, each contoured portion is preferably disposed in spaced relation to at least one end of the corresponding contoured segment. In at least one preferred embodiment the contoured portion is intermediately disposed between the opposite ends of the contoured segment. Interconnection of each contoured segment to the base segment of the support assembly is defined by a fixed, integral or removable attachment of one of the opposite ends of the contoured segment to a corresponding end or other appropriate portion of the base segment. As set forth above, the same base segment of the support assembly may be utilized to support and properly position at least two contoured segments. When this embodiment of the fixator assembly is utilized, opposite ends of the base segment are fixedly, integrally or removably secured to a corresponding end of each of the elongated contoured segments. Further, when so connected, each of the two contoured segments are operatively positioned on substantially opposite sides of the ankle area and in spaced but adjacent relation thereto. As such, corresponding ones of the contoured portions of each contoured segment extends transversely outward from the length of the corresponding contoured segment and along the height or length of the ankle area.

Another feature of the various preferred embodiments of the fixator assembly of the present invention, whether utilizing one or more contoured segments, is the ability to connect one or more transfixion pins or like transfixion members to the one or more contoured segments. When connected to the contoured segment(s) in the intended manner, the transfixion pin(s) or member(s) extends transversly inward, towards the affected portions of the ankle area, from the contoured segment to which it is attached into stabilizing engagement with the bone or other tissue associated with the ankle area at various points along the height or length of the ankle area. Further, each of the one or more transfixion pins can be connected to a contoured segment at a plurality of different locations along the length thereof including, but not limited to, a plurality of locations along the length of the contoured portion of the corresponding contoured segment. The angular and/or convergent configuration of the contoured portion provides significant versatility in positioning each of the one or more transfixion pins or members at any one of a plurality of different locations each representing an orientation having a different height or length relative to the ankle area.

Therefore, the positioning of the transfixion pin(s) or member(s) into stabilizing engagement with intended tissue of the ankle area, in the manner described herein, eliminates or significantly reduces the need for conventional support blocks or clamps to connect the transfixion pin(s). As set forth above, the use of such known devices and procedures for orienting the transfixion pins relative to a predetermined body part is time consuming and has a tendency to obscure X-rays or other viewing facilities of the body part. Therefore the use of the various preferred embodiments of the present invention eliminate or significantly reduce such known and well recognized disadvantages.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 3 is a side view of one of a possible plurality of contoured segments, normally intended for operative placement on the medial side of the ankle area and comprising a part of the support assembly along with the base segment as represented in FIG. 2.

FIG. 4 is a side view of another embodiment of one of a possible plurality of contoured segments, normally intended for placement on the lateral side and comprising a part of the support assembly of the present invention.

Like reference numerals refer to like parts throughout the several views of the drawings.

DETAILED DESCRIPTION OF THE PREFERRED EMBODIMENT

Figure 1:
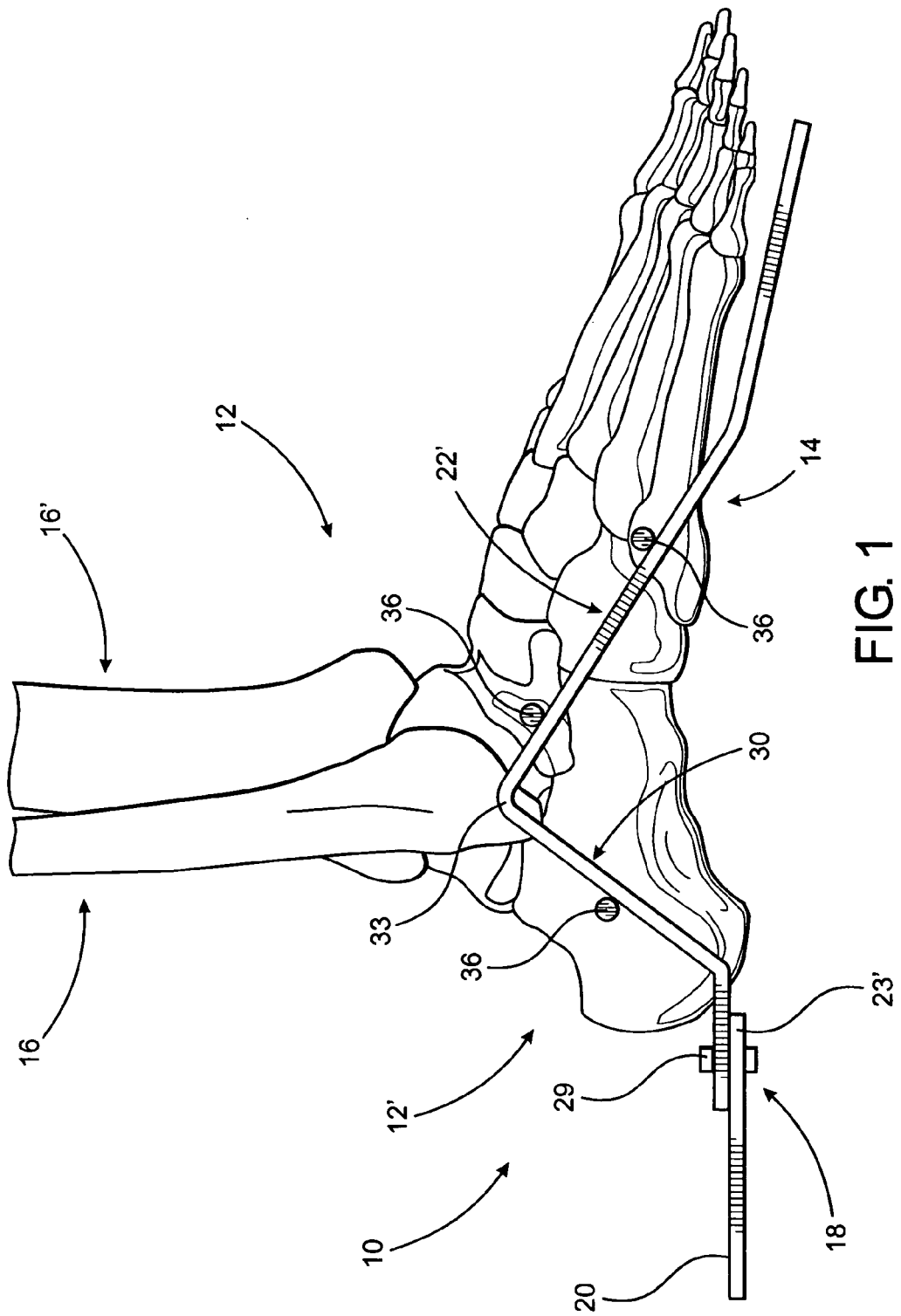
FIG. 1 is a side view in partial cutaway and schematic form of the external fixator assembly of the present invention operatively positioned relative to an ankle area of a patient.

As represented in the accompanying figures, the present invention is directed to an external fixator assembly generally indicated as 10. As demonstrated, the fixator assembly 10 is structured to be operatively positioned and used in a location substantially adjacent to the ankle area 12 of a patient, as best represented in FIG. 1. As set forth above, the ankle area 12 is meant to be descriptive of substantially the entire area represented in FIG. 1, which includes the ankle joint, foot, corresponding portions of the leg bones, including the fibula and tibia, as well as the associated components and tissue. In addition, the terms "height" and "length" of the ankle area 12 are used synonymously herein and refer to the distance from substantially the bottom of the foot, as at 14, to at least a portion the long bones of the leg, as at 16.

Figure 2:
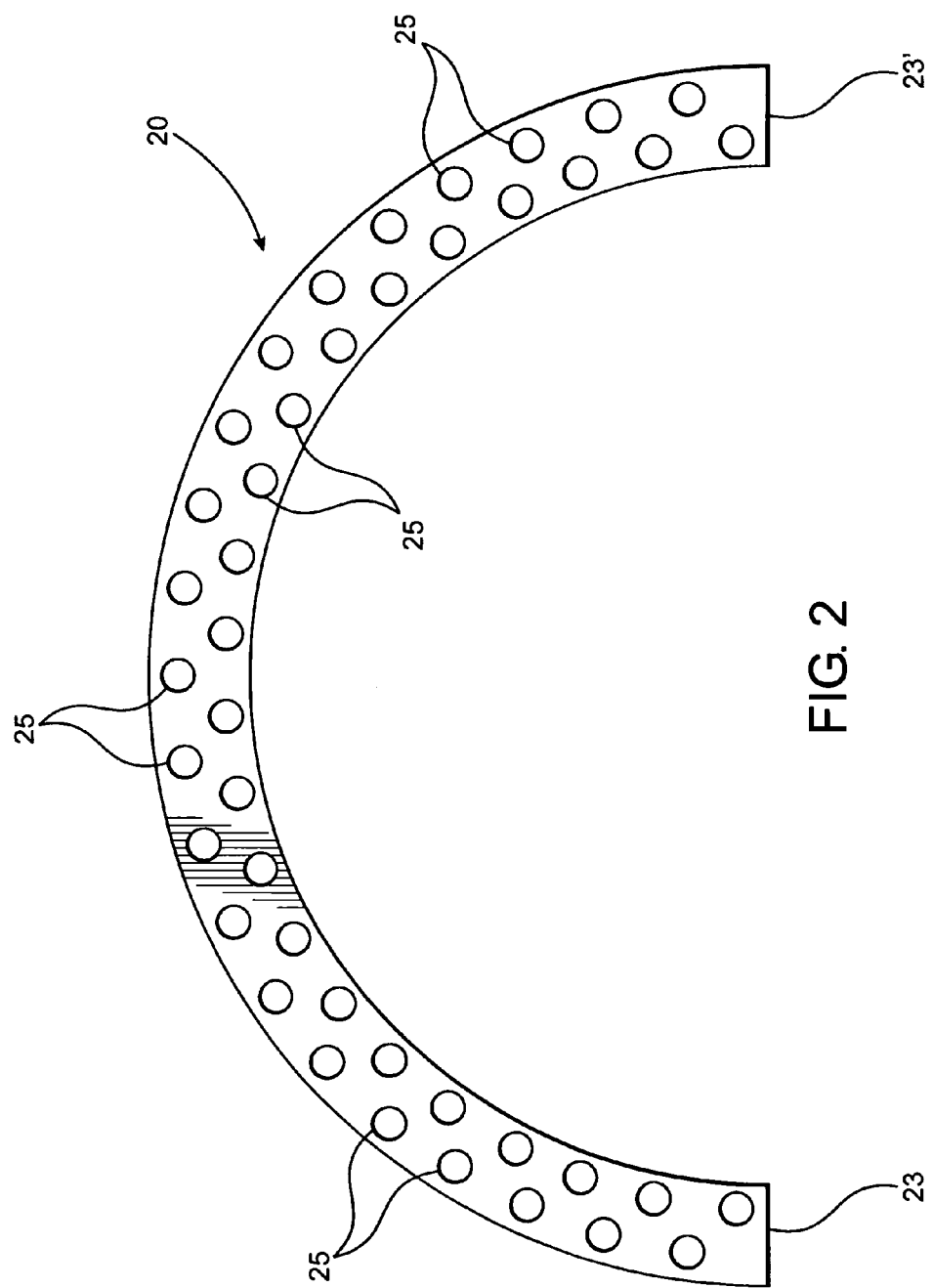
FIG. 2 is a top view of a base segment of a support assembly of the preferred embodiment of FIG. 1.
Figure 7:
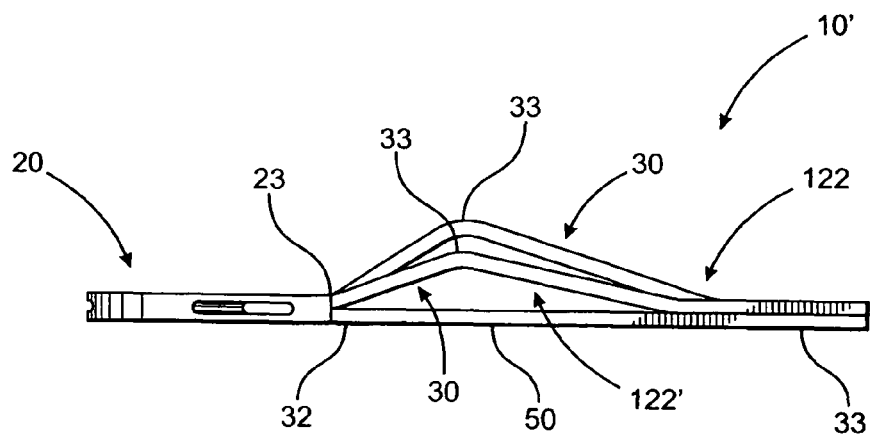
FIG. 7 is a side view of the embodiment of FIG. 6.

Accordingly, the external fixator assembly 10 comprises a support assembly generally indicated as 18 and including a base segment 20 and at least one contoured segment generally indicated as 22. As will be apparent in the description of the fixator assembly 10 hereinafter provided, the support assembly 18 may include more than one contoured segment 22 as schematically represented in FIG. 7 wherein two contoured segments 22 and 22' are operatively positioned relative to the ankle area 12. Further, the one or more contoured segments utilized may be selected from a larger plurality of contoured segments 22, 22', etc., which may differ from one another at least in dimension and configuration, as will be explained in greater detail hereinafter. With primary reference to FIG. 2, the base segment 20, defining at least a portion of the support assembly 18, preferably includes a curvilinear configuration which may be more specifically defined by an arcuate or semicircular shape. As such, the base segment 20 terminates in oppositely disposed free ends 23 and 23'. Further, a plurality of apertures or other appropriate structure 25 are positioned substantially along the length of the base segment 20 and are provided to facilitate connection of one or more struts to the base segment 20 preferably using fixation bolts, which are not shown for purposes of clarity. Such struts and interconnecting fixation bolts are well-known in the medical profession and are used to support and/or dispose the base segment 20 in a stabilized position relative to the ankle area 12. The opposite ends of such struts, to which the base segment 20 is connected, may be secured to a halo-type ring located above the ankle area 12 along the length of the leg and in surrounding relation to the bones 16' of the leg 16. The halo-type support ring is also well-known in the medical profession and is structured to have a plurality of transfixion pins secured thereto so as to extend radially inward into a firm connection with the bone(s) 16' of the leg 16. Such anchoring of the halo ring provides stabilizing support to the base segment 20 by virtue of the interconnection between the halo ring and the base segment 20 by the plurality of strut members, as is well-known.

Accordingly, as represented in FIGS. 1, 3, 4 and 5, the base segment 20 is disposed in at least partially surrounding but spaced relation to a portion of the ankle area 12, such as in the vicinity of the heel 12'. For purposes of clarity, the plurality of apertures or like connecting facilities 25 are not pictured in FIG. 5 but are intended to be present therein during the actual practical application or use of the fixator assembly 10. With further reference to both FIGS. 1 and 5, operative placement and use of the fixator assembly 10 comprises the supported disposition of at least one contoured segment 22 or 22' adjacent to an appropriate side of the ankle area 12. More specifically, contoured segment 22', having the smaller or lesser protruding contoured portion 30 is normally placed adjacent the lateral side of the foot and/or ankle area 12. In cooperation therewith, the contoured segment 22, having the larger or greater outwardly protruding portion 30 is normally appropriately positioned adjacent the medial side of the foot and/or ankle area 12.

Figure 5:
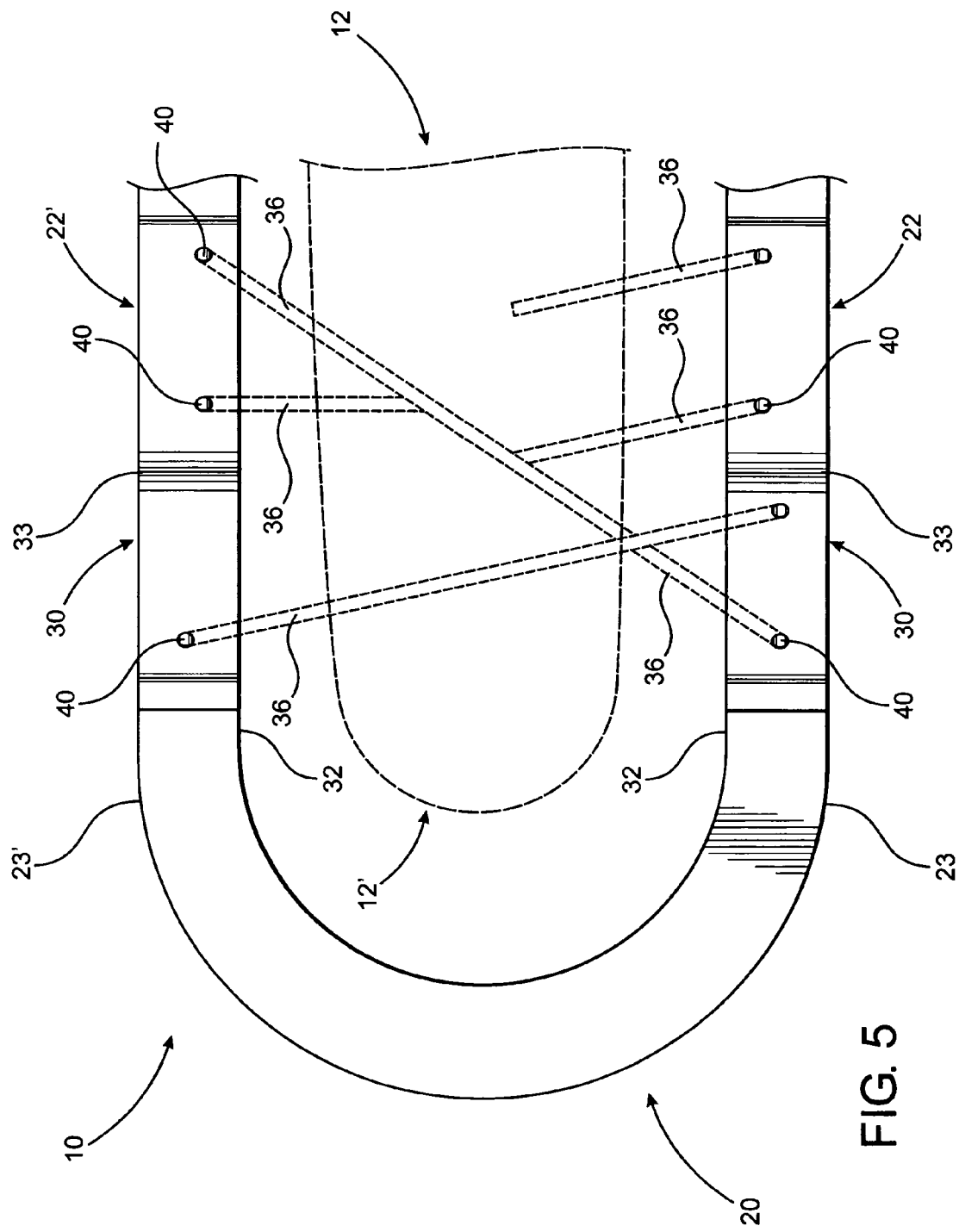
FIG. 5 is a top view in partial cutaway and schematic form of the fixator assembly of the present invention operatively positioned relative to the foot or lower leg portion of an ankle area of a patient.

As represented in FIG. 5, operative disposition and use of the fixator assembly 10 may comprise utilization of two of the contoured segments 22 and 22', wherein each is connected to correspondingly disposed ends 23 and 23' of the base segment 20. It is noted that the interconnection of the one or more contoured segments 22 and 22' to the base segment 20 may be removably connected, in a stable manner, through the use of appropriate connectors as at 29. Alternatively, one or both of the contoured segments 22 and 22' may be integrally or otherwise fixedly and therefore not removably secured to the base segment 20 in a manner which does not facilitate their disconnection from the base segment 20.

With primary reference to FIGS. 3 and 4, structural details of each of a plurality of contoured segments 22, 22', 22'', 22''', etc. are represented, wherein it is emphasized that common structural features do exist between each of a plurality of contoured segments 22, 22', etc. However, each of a possible larger number of contoured segments 22, 22', etc. may vary in dimension and configuration to accommodate accurate placement of a plurality of transfixion wires or members 36 relative to different ankle area 12 of different patients. Accordingly, it is emphasized that a large number of contoured segments may be made available to the involved medical personnel. This allows the appropriately dimensioned and configured contoured segment(s) to be selected and operatively utilized in different applications. Moreover, once selected, the one or more contoured segments 22, 22', etc. are dimensioned and configured to properly position the required transfixion wires, pins or members 36 based, at least in part, on the needs of specific patient. The larger number of contoured segments which may be provided also allows the medical personnel to quickly and easily choose an appropriately dimensioned and configured contoured segment to be used on an ankle area 12 of a patient dependent on the size and shape of that portion of a patient's body as well as a particular bones or other tissue which must be stabilized or otherwise treated.

Accordingly, each of the contoured segments 22, 22', etc. includes a contoured portion generally indicated as 30 disposed in spaced relation to at least one end 32 thereof, but more practically in spaced relation to opposite ends 32 and 32' thereof. As such, the contoured segment 30, in at least one preferred embodiment of the fixator assembly 10, is disposed intermediate the opposite ends 32 and 32'. Also, one of these opposite ends, such as at 32, is fixedly or removably connected to a correspondingly disposed end 23 of the base segment 20. Further, each of the contoured segments 22, 22', etc. comprise the contoured portion 30 having a substantially angular configuration as it protrudes transversely outward from a remainder of the length of the corresponding contoured segment 22, 22', etc. Moreover, the angled configuration of each of the contoured segments 30 may be more specifically defined by a substantially convergent configuration as each of the contoured portions 30 extend transversely outward from a remainder of the corresponding contoured segment 22 and 22'. Moreover, each of the contoured portions 30 terminates at what may be generally referred to as an apex or upper portion of the contoured segment 30, as at 33. Therefore, when one or more of the contoured segments 22, 22', etc. are operatively positioned as represented in FIGS. 1 and 7, a contoured portion 30 of each of the one or more contoured segments 22, 22', etc. extends transversely outward from a remainder of the corresponding contoured segment 22 or 22' along the height or length of the ankle area 12 as best demonstrated in FIG. 1. Accordingly, each of the contoured segments 22, 22', etc. are structured to be connected to and support one or more of a plurality of transfixion members or transfixion wires 36, as represented in FIGS. 1 and 5. As such, each of the one or more transfixion wires or pins 36 extend transversely inward, toward the appropriate portion of the ankle area 12, from any one of a plurality of possible locations on the contoured segment 22, 22', etc. including, but not limited to, being connected to the contoured portion 30 or other portions of the length of the corresponding contoured segment.

Further, due to the fact that the dimension and overall configuration of each of the contoured segments 22, 22', etc. may vary, the plurality of transfixion wires, pins or like members 36 may be located at different heights such that they will extend transversely inward into engaging relation with intended bone tissue or other tissue components of the ankle 12 as represented in both FIGS. 1 and 5. This versatile placement of the transfixion members 36 allows for the accurate and efficient stabilizing engagement of the transfixion members 36 with the bones or other components of the ankle area 12. More specifically, each of the transfixion members 36 may be located at different orientations along the height or length of the ankle area 12 so as to securely engage or stabilize different tissue portions of the ankle area 12 as required for healing and/or stabilization.

Therefore, it is emphasized that any of a larger plurality of contoured segments 22, 22', etc. may be available to medical personnel to facilitate the application to ankle areas 12 of different sizes and/or where different bones or like tissue must be engaged by the transfixion members 36. The differing size and/or configuration of the plurality of contoured segments 22, 22', etc. is clearly represented in FIGS. 3 and 4. As disclosed, the contoured portions 30 of the different contoured segments 22 and 22' have the aforementioned angular configuration which may be more specifically defined by a substantially convergent configuration. However, the contoured portions 30 may differ in height and or placement along the length of the corresponding contoured segment. As such, the transversely outward location of the apex 33 may differ in the plurality of contoured segments collectively represented as 22 and 22' in FIGS. 3 and 4.

As such, the contoured portions 30 of each of the contoured segments 22 and 22' will be located adjacent and in operative relation to an at least minimally different portion of the various bones or other tissue of the ankle area 12. This in turn will facilitate and enhance the versatility of accurately and efficiently placing one or more transfixion wires, pins or like members 36 into engaging, stabilizing relation to the intended bones or other tissue of the ankle area 12. More specifically, as each of the contoured portions 30 of each contoured segment 22, 22', etc. extend transversely outward from the remainder of the length of the corresponding contoured segments 22, 22', etc., the transversely inward ability to position one or more of the transfixion members 36 into engaging relation with appropriate tissue of the ankle area 12 as represented by a comparison of the FIGS. 1 and 5.

It is further emphasized that at least in one preferred embodiment represented in FIG. 7, the use of two contoured segments 22 and 22' may be typically accomplished by placement of each contoured segment 22 and/or 22' on appropriate and/or lateral and medial sides respectively of the ankle area 12. In this embodiment corresponding ends 32, 23 and 32, 23' of the contoured segments 22, 22' and base segment 20 respectively are fixedly or removably connected to one another. However, a variance in the dimension and configuration of the base segment may serve to alter the position of each or both of the contoured segments 22 and 22' relative to the ankle area 12 and/or to one another, from that represented in FIG. 5. In addition, a fixed or integral connection between the base segment 20 and one or more of the contoured segments 22 and 22' allows the medical personnel to choose an appropriate size and configuration of the support assembly 18 defined by the base segment 20 and one or more of the non-detachable contoured segments 22 and 22'. As such, a supply of the fixator assemblies 10 may be made available to medical personnel in predetermined and different sizes and configurations. This would alleviate the necessity of the medical personnel having to interconnect one or more of the contoured segments 22 and 22' to the base segment 20, such as by use of the connectors 29.

Additional structural details of each of the plurality of contoured segments 22, 22', etc. include the provision of a plurality of apertures 40, or other appropriately structured connecting sites, along the length of the contoured portion 30 as well as the remainder of the length of the corresponding contoured segment 22, 22' etc. These apertures 40 facilitate the interconnection of the one or more transfixion members 36 thereto, such that the one or more transfixion members 36 may be located at any one of a plurality of locations along the contoured portion 30 as well as the remainder of the length of the contoured segment 22, 22', etc. This further adds to the versatile and accurate placement of the transfixion member 36 along the entire length of the corresponding contoured segments 22, 22', etc. Also, when each of the contoured segments 22, 22', etc. are fixedly but removably connected to the appropriate ends as at 23 and 23' of the base segment 20, additional apertures or other appropriate structures may be provided to facilitate placement of an appropriate connector 29, as represented in FIG. 1. It is further emphasized that when two contoured segments are used, as in the embodiment of FIG. 5, they may comprise different or substantially equivalent dimensions and configurations, dependent on the medical requirements in the stabilization or other treatment of the ankle area 12.

Figure 6:
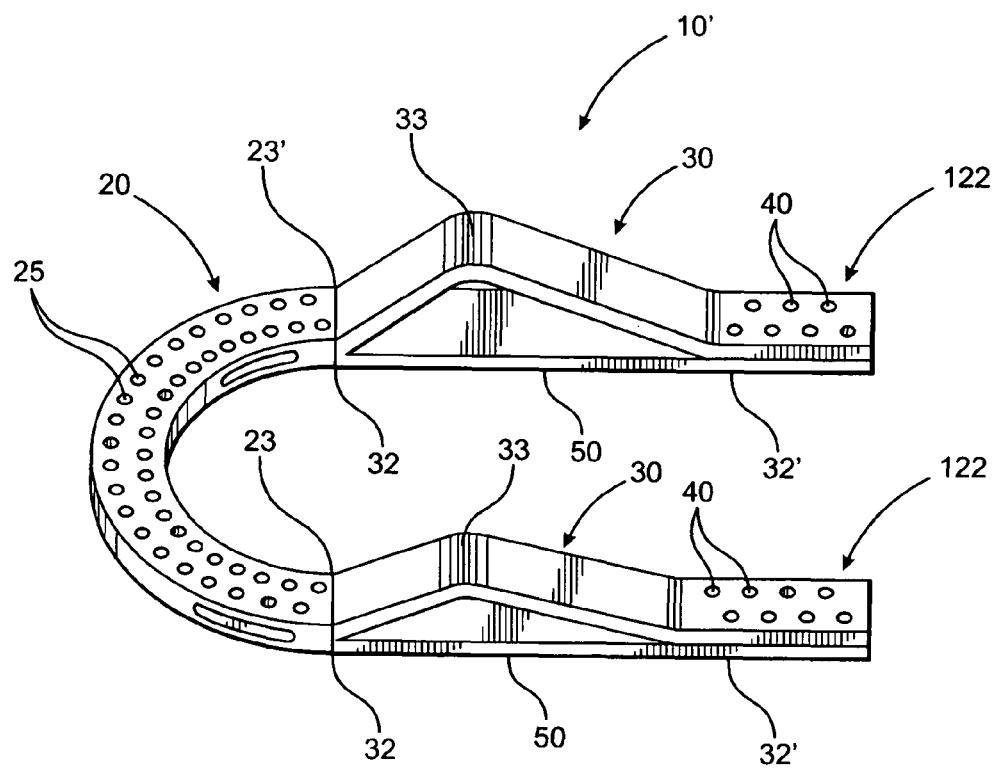
FIG. 6 is a top perspective view in partial cutaway of another embodiment of the external fixator assembly of the present invention.

Yet another preferred embodiment of the external fixator assemble is represented in FIGS. 6 and 7 and generally indicated as 10'. As such, the fixator assembly 10' includes a base segment 20 and at least one or, as set forth above, a plurality of at least two contoured segments 122 and 122'. Further, each of the contoured segments 122 and 122' include the contoured portion 30 extending transversely outward from a remainder of the length of the respective contour segments 122 and 122'. Also, each of the contoured portions 30 include what may be generally referred to as an apex 33. As indicated in the additional embodiments of the present invention described above, each of the one or more contoured segments 122 and/or 122' may be fixedly and/or integrally connected to the base segment 20 by connecting correcting ends 23', 32 as relates to the contoured segment 122. Similarly the contoured segment 122' may be fixedly and/or integrally connected at corresponding ends 23, 32 as indicated in FIG. 6. Alternatively, as also described with regard to the above noted embodiments, the contoured segments 122 and 122' may be removably connected to corresponding ends of the base segment 20 by appropriate connectors 29, as generally referred to FIG. 1.

In addition, the base segment 20 may include a plurality of apertures or like connecting sites 25 extending along the length thereof. Somewhat similarly, the length of the contoured segments 122 and 122' include connecting apertures or like connecting site structures 40 along their lengths, as well as along the length of the contoured portions 30 in the manner represented in FIG. 1.

Additional structural modifications present in the embodiment of FIGS. 6 and 7 include intermediate segment 50 disposed in interconnecting relation between opposite ends 32 and 32' of each of the contoured segments 122 and 122'. Further, the intermediate segments 50 of each of the contoured segments 122 and 122' are preferable disposed in spaced relation to and generally beneath or in underlying relation to the corresponding contoured portions 30, when the corresponding contoured segments 122 and 122' are in the orientation represented in FIGS. 6 and 7. Moreover, the intermediate segments 50 are disposed and structured to provide additional support, structural integrity and stability to the respective contour segments 122 and 122'. Further, connecting aperture or sites 40 may also be located along the length of the intermediate segment 50 of each of the contoured segments 122 and 122', so as to facilitate the connection or mounting of transfixion pins, wire or like members, as they extend transversely inward from the corresponding intermediate segment 50 into and towards the ankle assembly 12, as schematically represented in FIG. 5.

For purposes of clarity in further describing the intended disposition and structure of the intermediate segment(s) 50, additional schematic representations are presented in FIGS. 3 and 4, in phantom lines. However, it is emphasized that the embodiments of the contoured segments 22 and 22' as originally described, are absent the schematically represented intermediate segments 50. Moreover, in the schematic representation presented in phantom lines, the intermediate segments 50 are disposed in spaced relation beneath the corresponding contoured portions 30 and along the length thereof and in axially aligned, interconnecting relation between the remaining end portions 32 and 32'.

Additional structural features of the embodiments of FIGS. 6 and 7 include the intermediate segments 50 preferably being integrally formed with the remaining opposite ends 32 and 32' of the respective contoured segments 122 and 122'. However, other means of mounting, connecting and otherwise structuring the intermediate segments 50 relative to the remaining length and ends 32 and 32' of the contour segments 122 and 122' may be appropriate, provided that the strength, stability and structural integrity of the contoured segments 122 and 122' are appropriately enhanced.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A fixator assembly structured for placement adjacent an ankle area of a foot of the body, said fixator assembly comprising:
    a support assembly disposed adjacent the ankle area and structured to support at least one transfixion member in operative engagement with a predetermined portion of the ankle area,
    said support assembly including at least one base segment and at least one elongated contoured segment connected to said base segment,
    the one transfixion member connected to said one contoured segment and said contoured segment including a contoured portion disposed along an extending transversely outward from the length of said one contoured segment and along the length of the ankle area,
    said contoured portion comprising an angular, outwardly protruding, convergent configuration at least partially defined by an apex representing the maximum outward extension of said contoured portion, and
    said one contoured segment and said contoured portion extending along one lateral side of the foot, said one contoured segment and said contoured portion disposed and structured to dispose the at least one transfixion member at any one of a plurality of different orientations along the one lateral side of the foot relative to the ankle area.

2. A fixator assembly as recited in claim 1 wherein said contoured segment is removably connected to said base segment.

3. A fixator assembly as recited in claim 1 wherein said contoured segment is fixedly connected to said base segment.

4. A fixator assembly as recited in claim 1 wherein said contoured segment comprises oppositely disposed ends, said contoured portion disposed in inwardly spaced relation to at least one of said opposite ends.

5. A fixator assembly as recited in claim 4 wherein said contoured portion is disposed intermediate said opposite ends.

6. A fixator assembly as recited in claim 1 wherein said contoured segment comprises oppositely disposed ends, said contoured portion disposed in outwardly protruding, transverse relation to said ends.

7. A fixator assembly as recited in claim 6 wherein said convergent configuration is disposed and structured to connect the at least one transfixion member at any one of a plurality of locations between said opposite ends and along the length of said ankle.

8. A fixator assembly as recited in claim 7 wherein said contoured portion is disposed in spaced relation to at least one of said opposite ends.

9. A fixator assembly as recited in claim 8 wherein said contoured segment is structured to connect the at least one transfixion member at any one of a plurality of spaced apart locations along a length of said contoured portion and a remainder of said contoured segment.

10. A fixator assembly as recited in claim 6 wherein said base segment is connected to one of said opposite ends of said contoured segment.

11. A fixator assembly as recited in claim 10 wherein the other of said opposite ends of said contoured segment defines an unconnected free end thereof.

12. A fixator assembly as recited in claim 1 further comprising at least two contoured segments each connected to said base segment and operatively disposed adjacent different lateral sides of the ankle area.

13. A fixator assembly as recited in claim 12 wherein each of said contoured segments include a contoured portion disposed along an extending transversely outward from a length thereof.

14. A fixator assembly as recited in claim 13 wherein each of said contoured portions comprise a different angular configuration disposed at a different height along the length of a corresponding contoured segment.

15. A fixator assembly as recited in claim 12 wherein at least one of said contoured segments is removably connected to said base segment.

16. A fixator assembly as recited in claim 1 wherein said one contoured segment further comprises an intermediate segment disposed in spaced, underlying relation to said contoured portion and in interconnecting relation between remaining end portions of the length of said one contoured segment.

17. A fixator assembly as recited in claim 16 wherein said intermediate segment is disposed in substantially axially aligned relation with said remaining end portions of said one contoured segment.

18. A fixator assembly as recited in claim 17 wherein said intermediate segment is integrally attached to said remaining end portions.

19. A fixator assembly structured for use adjacent the ankle area of a foot of the body, said fixator assembly comprising:
    a support assembly disposed adjacent the ankle area and structured to support at least one transfixion member in operative engagement with a predetermined portion of the ankle area,
    said support assembly including at least one base segment and at least one elongated contoured segment connected to said base segment,
    said one contoured segment including a contoured portion disposed along and extending transversely outwardly from said contoured segment and along a length of the ankle area,
    said one contoured portion comprising an angular, outwardly protruding convergent configuration at least partially defined by an apex representing the maximum outward extension of said one contoured portion,
    said one contoured segment and said contoured portion extending along one lateral side of the foot, said one contoured segment connected to the at least one transfixion member at any one of a plurality of spaced apart locations along a length of said contoured portion and a remainder of said contoured segment, and said contoured portion structured and configured to dispose the at least one transfixion member in a transversely inward orientation into engagement with the ankle area from any one of a plurality of locations along a length of the one lateral side of the foot of the ankle area.

20. A fixator assembly as recited in claim 19 wherein said contoured segment is removably connected to said base segment.

21. A fixator assembly as recited in claim 19 wherein said contoured segment is fixedly connected to said base segment.

22. A fixator assembly as recited in claim 19 wherein said one contoured segment further comprises an intermediate segment disposed in spaced, underlying relation to said contoured portion and in interconnecting relation between remaining end portions of said one contoured segment.

23. A fixator assembly as recited in claim 19 wherein said intermediate segment is disposed in substantially axially aligned relation with said remaining end portions of said one contoured segment.

24. A fixator assembly as recited in claim 19 wherein said intermediate segment is integrally attached to said remaining end portions.

25. A fixator assembly as recited in claim 19 further comprising at least two contoured segments each connected to said base segment and operatively disposed adjacent different lateral sides of the ankle area; each of said contoured segments including a contoured portion disposed along and extending transversely outward from a length of a corresponding one of said contoured segments; each of said contoured portions comprising an angular, outwardly protruding convergent configuration at least partially defined by an apex representing the maximum outward extension of corresponding ones of said contour portions, each of said contoured segments structured to connect and dispose at least one transfixion member along a corresponding lateral side of the foot and at any one of a plurality of spaced apart locations along a length of said contoured portion and a remainder of said contoured segment.

26. A fixator assembly as recited in claim 25 wherein each of said two contour segments comprises an intermediate segment disposed in spaced, underlying relation to said contoured portion and in interconnecting relation between remaining end portions of the length of said corresponding contoured segment.

27. A fixator assembly as recited in claim 25 wherein each of said intermediate segments is disposed in substantially axially aligned relation with said remaining end portions of said corresponding contoured segment.

28. A fixator assembly as recited in claim 25 wherein each of said intermediate segments is integrally attached to said remaining end portions of said corresponding contoured segment.

29. A fixator assembly as recited in claim 25 wherein each of said contoured portions comprise a different angular configuration.

30. A fixator assembly as recited in claim 19 wherein said base segment comprises a substantially semi-circular configuration and is disposed at a different height along the length of the corresponding contoured segment.

* * * * *